United States Patent [19]

Bunel

[11] Patent Number: 5,324,851
[45] Date of Patent: Jun. 28, 1994

[54] RECOVERY OF PALLADIUM CATALYST

[75] Inventor: Eimilio E. Bunel, Wilmington, Del.

[73] Assignee: E. I. du Pont de Nemours and Company, Wilmington, Del.

[21] Appl. No.: 136,271

[22] Filed: Oct. 14, 1993

[51] Int. Cl.$^5$ .............................................. C07F 15/00
[52] U.S. Cl. ..................................... 556/136; 556/137
[58] Field of Search ................................. 556/136, 137

[56] References Cited

U.S. PATENT DOCUMENTS

| | | | |
|---|---|---|---|
| 3,054,746 | 9/1962 | Gaden, Jr. et al. | 210/44 |
| 3,437,431 | 4/1969 | Platz et al. | 23/50 |
| 4,290,767 | 9/1981 | Campbell et al. | 260/429 R |
| 4,454,333 | 6/1984 | Jenck | 560/1 |
| 4,522,760 | 6/1985 | Jenck | 260/410.9 R |
| 5,026,901 | 6/1991 | D'Amore | 560/207 |
| 5,099,047 | 3/1992 | Sato et al. | 556/136 |

Primary Examiner—Jose'G. Dees
Assistant Examiner—Porfirio Nazario-Gonzalez

[57] ABSTRACT

Palladium catalyst is recovered from an organic solution by extraction with water/base solution. The water/base solution is then neutralized, and the palladium extracted with an organic solvent. The tramp metals remain in the water phase.

5 Claims, No Drawings

RECOVERY OF PALLADIUM CATALYST

FIELD OF THE INVENTION

This invention relates to the recovery of palladium catalyst contained in an organic solution.

BACKGROUND OF THE INVENTION

Many processes have been disclosed in which transition metal catalyst are used to carbonylate olefins. In particular, palladium-catalyzed carboalkoxylation reactions have been studied for many years as a means of converting butadiene to adipic acid precursors. U.S. Pat. No. 5,026,901 to D'Amore discloses a process for the preparation of linear alkyl pentenoates by reacting butadiene, carbon monoxide, and an alkyl alcohol in an organic solvent with a palladium catalyst.

Palladium catalysts have been recovered from carboalkoxylation of dienes by the addition of onium salt: see U.S. Pat Nos. 4,454,333 and 4,522,760.

SUMMARY OF THE INVENTION

The present invention is a process for the recovery of palladium from a water-immiscible organic solution containing dissolved palladium and dissolved corrosion (tramp) metals which comprises (a) contacting the water-immiscible organic solution with an aqueous solution of a base selected from the group consisting of amines and inorganic bases, (b) separating the aqueous solution now containing dissolved palladium and corrosion (tramp) metals from the water-immiscible organic solution, (c) neutralizing the aqueous solution with acid and contacting the aqueous solution with a water-immiscible organic solvent for palladium, and (d) separating the water-immiscible organic solvent for palladium now containing dissolved palladium from the aqueous solution containing the corrosion (tramp) metals.

The process of the invention is particularly useful in recovering palladium from a water-immiscible organic solution which contains a major amount of dimethyladipate. Usually the aqueous solution of a base of step (a) contains 0.5% to 10% parts by weight of base.

Often the tramp metals are chromium, nickel, iron, and molybdenum.

DETAILED DESCRIPTION

Palladium can be easily recovered from water-immiscible organic solutions (process solutions) by extracting it with a base/water solution under very mild conditions (atmospheric pressure and at about room temperature, i.e. 25 degrees C.). Also, corrosion metals are extracted into the base/water solution. A variety of bases are suitable for the extraction: amines such as ammonia, aliphatic (C1 to C8) primary amines and aromatic primary amines, secondary amines (C1 to C4), heterocyclic amines and diamines, aliphatic and aromatic diamines and inorganic bases such as hydroxides of sodium, potassium, rubidium, cesium, magnesium, calcium and barium.

The base/water solution containing the palladium catalyst is then separated from the organic stream for example by decantation, and is then neutralized to a pH of about 7 with a suitable acid, for example hydrochloric acid, hydrofluoric acid, hydrobromic acid, hydriodic acid, acetic acid or propionic acid. Then the palladium is extracted from the water solution with a water-immiscible organic solvent for palladium leaving the corrosion metals in the aqueous layer. The organic solvent for palladium may be the same solvent as contained in the process solution, or it may be a different water-immiscible organic solvent for palladium.

Suitable water-immiscible solvent to include: aromatic solvents (benzene, toluene, xylenes); halogenated solvents (chloroform, dichloromethane, dichloroethanes, trichloroethanes, tetrachloroethanes, chlorobutenes, allyl chloride), aliphatic and aromatic esters (dimethyl adipate, dimethyl succinate, ethyl acetate, methyl-3-pentenoate, methyl benzoate).

The process of the invention is applicable to the recovery of soluble palladium catalysts including $PdX_2$ (X=Cl, Br, I); Pd(acetate)$_2$; Pd(PPh$_3$)$_4$; Pd(CO$_2$CH$_3$Cl(PPh$_3$)$_2$; PdCl$_2$(PPh$_3$)$_2$ and derivatives thereof.

Another application of the extraction procedure described herein is in the catalyst recovery from continuous operation. The more volatile components of the reaction mixture, including the products of the process, are separated by distillation, while the catalyst accumulates in the higher boiling distillation residue. Although the high boiling residue may be recycled to the process, it is not possible to return the entire amount. It is highly desirable to recover the catalyst from the high boilers. The high boilers may then be disposed of and the catalyst recycled.

The major interest of this invention is in the selective recovery of palladium from process solutions that contains not only palladium but also corrosion metals.

DETAILED EXAMPLES

Example #1: Extraction of Pd and Corrosion Metals A solution containing:

2.49 gr. of [C$_4$H$_7$-Pd-Cl]$_2$
12.63 gr. of Chlorobutenes
29.61 gr. of Methanol
404.27 gr. of Dimethyl adipate was introduced into a 50 mL autoclave (Hastelloy-C) with exit dip tube fixed at a level so as to maintain 22.8 mL liquid volume, containing initially 22.8 mL of dimethyl adipate at 120 degrees C. under CO at a total pressure of 1500 psig. The solution was pumped into the autoclave at 12.8 mL/hr. Simultaneously, liquid butadiene was fed into the autoclave at 2.43 mL/hr. and CO was fed at 2.28 standard liters/hr. into the autoclave. The product collected continuously and kept under nitrogen atmosphere. Steady state was reached after 4.5 hrs and the composition (weight %) of the solution (herein after called Product Solution 1) at steady state was:

0.55% butadiene
0.03% Methanol
0.57% Chlorobutenes
0.03% Methyl 4-pentenoate
18.33% Methyl 3-pentenoate
0% Methyl 2-pentenoate
0.3% vinylcyclohexene
77.8% Dimethyl adipate 28.4 gr. of Product Solution 1 were combined with 5 gr. of water containing 135 mg of ethylenediamine. The organic layer was separated from the water layer (Solution A) and extracted again with 5 gr. of water containing 135 mg of ethylenediamine. The water phase was separated (Solution B) from the organic phase (Solution C). Palladium and corrosion metals analysis of the solutions A,B and C are:

| Solution | Pd [ppm] | Ni [ppm] | Mo [ppm] |
|---|---|---|---|
| A | 6065 | 133 | 29 |
| B | 727 | 13 | 4 |
| C | 0 | 2 | 0 |

Example #2: Selective Recovery of Pd 28.1 gr. of Product Solution 1 of Example 1 were extracted twice with 5 gr. of water containing 135 mg of ethylenediamine. The water solutions were combined into one water phase (Solution A). 10 gr. of toluene were mixed with solution A and 0.5 gr. of concentrated HCl were added. The toluene layer was separated (Solution B) and the water layer extracted again with 5 gr. of toluene (Solution C). Palladium and corrosion metals analysis of the solutions A, B and C are:

| Solution | Pd [ppm] | Cr [ppm] | Fe [ppm] | Ni [ppm] | Mo [ppm] |
|---|---|---|---|---|---|
| A | 341 | 23 | 25 | 22 | 41 |
| B | 2575 | 0 | 0 | 0 | 0 |
| C | 945 | 0 | 0 | 0 | 0 |

Example #3: (Control Example) Extraction of Pd does not work in the absence of base.

A Hastelloy-C autoclave (150 mL) was charged with:

0.80 gr of $(C_6H_5CN)_2PdCl_2$
3.0 gr of Chlorobutenes
10.3 gr of Methanol
120 gr of Toluene The reactor was assembled, pressured with carbon monoxide to 200 psi. Then, 16.8 g of butadiene were added. The reactor was pressurized to 1500 psi and heated to 120 degrees C. for 1 hour. A homogeneous brown-yellow solution (hereinafter called Product Solution 3) was recovered (148.14 gr). The GC analysis showed the following Composition ( weight %):
0.9% butadiene
0.56% methanol
0.2% Chlorobutenes
0% Methyl 4-pentenoate
12.6% Methyl 3-pentenoate
0.01% Methyl 2-pentenoate
0.13% vinylcyclohexene
0% dimethyl 2,3-dimethylsuccinate
0% Dimethyl 2-methyl-glutarate
0.7% Dimethyl adipate
84.9% Toluene 5 gr of Product Solution 3 were extracted first with 5 gr of water and then extracted three times with 5 gr of water containing 145 mg of ethylenediamine. The organic layer after the four extractions (Solution A) and the water layers (Solutions B, C, D and E respectively) were analyzed for palladium.

| Solution | Pd [ppm] |
|---|---|
| A | 9 |
| B | 58 |
| C | 859 |
| D | 43 |
| E | 2 |

Example #4: Example of a non-chelating amine 20 gr of a Product Solution 3 of Example #3 were extracted twice with 5 gr of water containing 290 mg of pyridine. The organic layer after the extractions (Solution A) and water layers (Solutions B, C) were analyzed for palladium.

| Solution | Pd [ppm] |
|---|---|
| A | 184 |
| B | 6843 |
| C | 3343 |

Example #5: (Control Example) Reversible Extraction without neutralization of amine 20 gr of Product Solution 3 of Example #3 were extracted with 5.38 gr of water containing 210 mg of pyridine. The water layer was extracted twice with 10 gr of toluene (Solutions C and D respectively). All the solutions (A, B, C, D and E) were analyzed for palladium.

| Solution | Pd [ppm] |
|---|---|
| A | 2999 |
| B | 1020 |
| C | 1650 |
| D | 1090 |
| E | 1740 |

Solution A: original product solution
Solution B: original product solution after extraction with water/pyridine
Solution C: first toluene extraction
Solution D: second toluene extraction
Solution E: Water/pyridine solution after two extractions with toluene

What is claimed is:

1. A process for the recovery of palladium from a water-immiscible organic solution containing dissolved palladium and dissolved tramp metals which comprises (a) contacting the water-immiscible organic solution with an aqueous solution of a base selected from the group consisting of amines and inorganic bases, (b) separating the aqueous solution now containing dissolved palladium and tramp metals from the water-immiscible organic solution, (c) neutralizing the aqueous solution with acid and contacting the aqueous solution with a water-immiscible organic solvent for palladium, and (d) separating the water-immiscible organic solvent for palladium now containing dissolved palladium from the aqueous solution containing the tramp metals.

2. The process of claim 1 in which the water-immiscible organic solution of step (a) contains a major amount of dimethyladipate, and the aqueous solution contains ethylenediamine.

3. The process of claim 2 in which the water-immiscible organic solvent for palladium of step (c) is selected from the group consisting of toluene, benzene, chloroform, dichloromethane, tetrochloroethane, and chlorobutenes.

4. The process of claim 1 in which the aqueous solution of a base of step (a) contains 0.5% to 10% parts by weight of base.

5. The process of claim 1 in which the tramp metals are chromium, nickel, iron, and molybdenum.

* * * * *